United States Patent [19]

Lew et al.

[11] Patent Number: 5,599,583
[45] Date of Patent: Feb. 4, 1997

[54] ENCAPSULATION WITH WATER SOLUBLE POLYMER

[75] Inventors: Chel W. Lew, San Antonio, Tex.; Keith Branly, Brandon, Fla.; Jesse Gaytan, San Antonio, Tex.

[73] Assignee: Micro Flo Company, Mulberry, Fla.

[21] Appl. No.: 250,766

[22] Filed: May 27, 1994

[51] Int. Cl.⁶ .................. B01J 13/02; B05D 7/00; B32B 19/00
[52] U.S. Cl. .................. 427/213.3; 427/212; 428/357
[58] Field of Search .................. 427/213.3, 212; 428/357

[56] References Cited

U.S. PATENT DOCUMENTS

| | | | |
|---|---|---|---|
| 3,664,963 | 5/1972 | Pasin | 252/316 |
| 3,703,576 | 11/1972 | Kitajima et al. | |
| 4,629,621 | 12/1986 | Snipes | 424/19 |
| 4,806,337 | 2/1989 | Snipes et al. | 71/65 |
| 4,867,902 | 9/1989 | Russell | 252/186.32 |
| 5,073,295 | 12/1991 | Bruttel et al. | 252/301.19 |

FOREIGN PATENT DOCUMENTS

| | | |
|---|---|---|
| 2169316 | 9/1973 | France. |
| 9204891 | 4/1992 | WIPO. |

OTHER PUBLICATIONS

K. Thoma et al., "beziehungen sqischen herstellungsparametern und pharmazeutisch-technologischen anforderungen an biodegradierbare mikropartikeln", DIE Pharmazie, vol. 47, No. 2, Feb '92, pp. 115–119.

*Primary Examiner*—Nathan M. Nutter
*Attorney, Agent, or Firm*—Banner & Witcoff, Ltd.

[57] ABSTRACT

Molten, water soluble polymer is used as a binder for agriculturally effective active ingredients in a water free encapsulation process. For finely divided solid active ingredients, a solvent for the binder can be used to increase the amount of bound active ingredient. For water insoluble active ingredients, the binder provides a method for rendering the active ingredient dispersable in water.

15 Claims, No Drawings

ENCAPSULATION WITH WATER SOLUBLE POLYMER

FIELD OF THE INVENTION

The invention relates to agriculturally effective materials that are encapsulated with a water soluble, film-forming polymer and a nonaqueous, low temperature process for encapsulating such materials.

BACKGROUND OF THE INVENTION

Various methods have been used to present agriculturally effective active ingredients (AIs) in a solid form. The most common methods include spray drying and granulations.

Spray drying is performed typically by passing an aqueous slurry of ground AI and a binder material (usually a number of materials based on alkylnaphthylene or alkylformaldehyde condensate, calcium silicate, kaolinite, diatomaceous clays) through a nozzle into a tower. The droplets are dried at a temperature of about 150° C. As the water is vaporized, the slurry droplets form the particulate product and are collected. Despite the high temperature drying, contact between the slurry water and the amount of residual adsorbed water in the binder can degrade many agriculturally useful Ais during storage. Spray drying is can be performed with water insoluble Ais if an emulsion is first formed.

Granulation can be performed by spraying an AI onto a ground carrier. Other granulation processes include low pressure extrusion, briquetting, and pelletizing. The particle size from these processes is generally about 2000–4000 μm carrying 20 wt % or less of the AI.

Encapsulation is an alternative to spray drying and granulation that can provide a number of advantages for various active ingredients (Ais). In general, encapsulation in a binder can render Ais easy to handle, reduce or eliminate exposure concerns compared to the pure AI, as well as provide a measure of control over the rate, timing, and duration of AI release depending on the encapsulating material and the AI.

A product that is successfully encapsulated must consider a number of differing and often competing needs. For example, encapsulated baits must provide a structure and chemistry that considers the target insect or animal behavior, the application method, and any handling and environmental concerns for the AI. Each AI and intended can and often do result in differing encapsulation forms and formulations.

Polyethylene glycol (PEG) has generated some degree of interest in the art. PEG is a water soluble film-forming polymer that is commercially available in a wide variety of molecular weight solids. PEG has been used in a number of ways for the encapsulation of various Ais.

Pasin U.S. Pat. No. 3,664,963 describes the use of a PEG bath to remove solvent from particles containing an active ingredient, a solvent-soluble shell forming material, and a shell solvent that are sprayed into the PEG bath. As solvent is desorbed into the PEG, the shell forming material surrounds and encapsulates the active ingredient.

Snipes U.S. Pat. No. 4,629,621 and its continuation-in-part Snipes et al. U.S. Pat. No. 4,806,337 describe a cylindrical pill made by injection molding and having a controllable rate of release. In the pill is an active ingredient dispersed in a matrix containing 5–95% PEG and 5–95% of a water insoluble, amphophilic erosion rate modifier. The erosion modifier either slows the dissolution rate of the PEG to prolong the delivery period of the active ingredient or increases the dissolution rate for a faster release based on pH or moisture content of the surrounding system. The active ingredient is described generally as an ecological agent of an unspecified loading level, or "up to 70% by weight" of a pharmaceutical.

Russell U.S. Pat. No. 4,867,902 describes the use of PEG to encapsulate alkali metal superperoxides which release oxygen through the PEG binder. When formed into mats or fabrics, they are described as useful for filters in breathing masks. The encapsulation process involves the sequential steps of melting the PEG, mixing in the powdered chemicals, forming coatings or layers, and allowing the PEG to resolidify at room temperature. See, column 5, lines 22–61.

The use of PEG as a binder has been limited by the AI loading levels permitted by the molten PEG. Experience has shown that agricultural chemicals can be effectively loaded up to only about 55% by weight. Higher loading levels of AI would be useful to provide a more economic use of PEG binders for encapsulation and a smaller volume of encapsulated materials.

SUMMARY OF THE INVENTION

It is an object of the invention to provide a water dispersible, water dissolvable particle containing an agriculturally active ingredient bound by a water soluble, film-forming polymer.

It is another object of the invention to provide a dry, solid particle providing high levels of agriculturally active ingredients.

It is a further object of the invention to provide a process for forming a dry solid particle from an agriculturally active ingredient in a water soluble, film-forming polymer binder at a relatively low temperature and without the use of water in the process.

In accordance with these and other objects that will become apparent from the description herein, encapsulated compositions according to the invention are made of an agriculturally effective active ingredient homogeneously mixed throughout a water soluble, film-forming polymer. Preferably, the film-forming polymer is selected from the group consisting of: (a) polyethylene glycol; and (b) block copolymers of polyoxyethylene and polyoxypropylene.

In another aspect of the invention, the process of the invention comprises:

mixing until homogeneous an agriculturally effective active ingredient with a water-free, molten, film-forming polymer binder, wherein said molten binder exhibits a viscosity of less than about 1000 cp;

cooling the homogeneous mixture to a temperature above the solidification temperature of said homogeneous mixture; and forming said homogeneous mixture into particles by spraying the cooled mixture into a congealing zone at a temperature below the melting point of said polymer binder.

The present invention provides a water-free process conducted at low temperatures relative to prior water-based particle forming processes for forming dry solids from water and/or heat sensitive agriculturally active ingredients at loading levels higher than available with conventional granulation processes. In addition, the water soluble, film-forming polymer binder of the invention can be used to encapsulate water insoluble active ingredients that have been distributed only through the use of nonaqueous solvents. With the present invention, such water insoluble AIs can be dispersed in and distributed with aqueous media. The use of aromatic and other expensive nonaqueous solvents is thereby avoided.

DETAILED DESCRIPTION

The encapsulated compositions of the invention relate to an agriculturally effective active ingredient (AI) that is encapsulated by a water soluble, film-forming polymer in a water-free encapsulation process. Because the present encapsulation process is performed without the use of water, the invention is particularly suitable for those agricultural chemicals that are sensitive to hydrolysis or degradation in the presence of moisture. Similarly, the relatively low temperatures needed for melting the binder and dispersing the agricultural AI therein mean that the process is useful for AIs sensitive to high temperatures such as those typically found in spray drying processes.

Active Ingredients

Encapsulation according to the invention is particularly well suited for agricultural AIs that are water insoluble. The solubility of the PEG in water is used to permit the PEG to act as a solid dispersion vehicle for the water insoluble AI thereby allowing the use of an aqueous spray media. The present invention thus provides a vehicle whereby the need for nonaqueous carrier solvents is avoided with an associated reduction in cost and environmental impact.

Agrichemicals useful for PEG encapsulation by the invention include fungicides, insecticides, and herbicides in an amount within the range from about 1 wt % to about 99 wt %, preferably an amount within the range from about 20 wt % to about 90 wt %, and most preferably an amount within the range from about 50–90 wt %. With the present invention, water dispersible encapsulated AI can be prepared at relatively higher loading rates than with granules and without exposing the AI to the high temperature drying required for conventional spray drying processes.

Exemplary fungicides that can be encapsulated according to the invention include: captan; any of the EBDCs (e.g., mancozeb, maneb, niram, metiram, zineb, and ferbam); chlorothalonil; iprodione; ziram; copper salts (e.g., copper sulfate and copper oxychloride); and sulfur. The invention is particularly well suited for encapsulating captan in particles having 55–80 wt % captan therein.

Insecticides for encapsulation include ethion; ethyl parathion; diazinon; endosulfan; solid and liquid forms of the carbamates (e.g., carbaryl, aldicarb, methomyl, carbofuran, bendiocarb, oxamyl, thiodicarb, trimethylcarb); organophosphates (e.g., phorate, terbufos, fonophos, isofenphos, ethoprop, fenamiphos, disulfoton, malathion, parathion, demeton, dimethoate, chlorpyrifos, diazinon, azinphosm-ethyl, and phosmet); compounds which break down an insect's digestive tract tissue including fluorine compounds (cryolite), zinc, and mercury; nicotine; rotenone; neem oil or azadiractin; natural or synthetic pyrethrins; petroleum oils; the halogenated hydrocarbons (e.g., endrin, aldrin and its epoxide, dieldrin, heptachlor, DDT, BHC, lindane, chlordane, methoxychlor, DDD, TDE, and the polychlorinated biphenyls); and microbials (e.g., Bacillus thuringiensis and entomopathic viruses such as the bacculo viruses).

Herbicides that can be encapsulated include trifluralin; paraquat; glyphosate and salts thereof; alachlor; and the phenoxys as well as salts thereof (e.g., 2,4-D).

The Binders

The water soluble, film-forming polymer binder of the invention should be a non-tacky solid at room temperature and be chemically inert toward the AI being encapsulated. Polymer binders preferably exhibit a melting point within the range from about 35° C. to about 65° C. Solubility of at least 20% in alcohols, such as methanol or isopropyl alcohol, is a preferred test for determining chemical compatibility between binder and encapsulated AI. While not wishing to be bound by theory, the binders of the present invention appear to act as a wetting agent for the AI that permits the encapsulated material to be suspended in an aqueous dispersion system. Particles having an average diameter within the range from about 500 µm to about 1000 µm are particularly preferred.

The water solubility of the binder at 20° C. should be less than 100% soluble, preferably within the range from about 15 wt % to about 90 wt %. Solubility within this range permits the encapsulated AI to be mixed in an aqueous spray tank and sprayed therefrom without significant dissolution of AI in the tank. The residual moisture and additional moisture will dissolve the binder and release the AI.

The two preferred binders materials that exhibit the desired properties for the present invention are polyethylene glycol (PEG) and block copolymers of ethylene oxide and propylene oxide (EO/PO).

Polyethylene glycol useful in the present invention is commercially available in molecular weights ranging from 1,000 to 20,000 with melting points within the range of about −15° C. to 70° C. The PEG with a melting point within the range from about 37° C. to about 64° C. forms a nontacky, dry solid at room temperature that is particularly well suited as a binder for the present invention.

The EO/PO polymers are commercially available in a wide variety of physical and chemical characteristics from BASF Wyandotte Corporation, Performance Chemicals Division, Parsippany, N.J. U.S.A. under the PLURONIC™ name. These materials are sold as surfactants for emulsions, suspension stabilizers, and associative thickeners.

Solid or encapsulated forms of one or more spray adjuvants can be carried in the binder. Suitable adjuvants include spreader-stickers, nonionic surfactants (e.g., calcium dodecylbenzenesulfonate salts, nonyl and octyl phenolethoxylates, and alkyl naphthylene sulfonates), liquid emulsifiers (e.g., sorbitol esters), dispersing agents (lignin sulfonates and salts thereof), and ultraviolet screening agents (e.g., titanium dioxide, zinc oxide, carbon black, congo red, para-aminobenzoic acid, and the benzophenones). Preferably, the encapsulation binder contains a minimum amount of such additional components to maximize the amount of AI carried in the binder.

The Encapsulation Process

In the encapsulation process, finely divided or liquid AI is mixed into molten binder and formed into droplets. In general, finely divided AI solids must be first ground to size with conventional techniques if the AI is not commercially available in a pre-ground form. AI solids exhibiting a size of less than about 100/µm in diameter is well suited for the present invention. The invention is particularly useful for AI solids having a size within the range from about 0.1 µm to about 50 µm and even more useful for AI solids within the range of 2 µm to about 30 µm. As used herein, reference to AI solids includes active ingredients that naturally exhibit a solid form at room temperature as well as liquids that have been previously encapsulated or adsorbed in a solid carrier.

The AI is added to a molten binder containing any additives and mixed. Molten binder is preferably melted in a stirred, jacketed vessel to control the melting temperature. The molten binder preferably exhibits a viscosity of less than about 1000 cp, more preferably less than about 500 cp, and most preferably less than about 100 cp to allow particle formation through conventional nozzles and extrusion equipment.

If, after a solid active ingredient is added, the viscosity of the molten binder/AI mixture is found to be greater than about 500 cp, a solvent for the binder should be used to reduce viscosity. Any solvent is, however, preferably added to the molten binder before adding the AI solids. Such a solvent will depress the solidification point of the binder in proportion to the amount of solvent used, so some process adjustment may have to be made as noted below to solidify the solids. The solvent will, however, permit the binder to be loaded to levels of AI higher than otherwise possible without the solvent and will not adversely affect the performance of the product.

Solvents that can be used for reducing the viscosity of the PEG and increasing the loading rate of active ingredient include: alcohols (e.g., isopropyl alcohol, and methyl alcohol) acetone, CELLOSOLVE™ (made from butylcellulose); ethyl acetate, and toluene.

The encapsulation of liquid AIs does not generally need a solvent. The liquid AI will act as a solvent for the binder and reduce the viscosity accordingly. At some concentration level that is unique to each active ingredient, however, no additional. AI can be carried by the binder. Attempting to add more AI adversely affects the structural integrity of the resulting particle. At very high concentrations of AI, e.g. , greater than about 70 wt % for some materials, the amount of binder is insufficient to impart integrity to the microcapsule. An overloaded particle is friable and cannot maintain a structurally intact particle form with even moderate pressure thereby breaking apart and forming undesired fines. Rolling the formed particles between the thumb and forefinger with a moderate crushing pressure will readily reveal whether the loading limit of the binder has been exceeded.

The structural integrity of the particle can be enhanced by adding to the molten binder a second film-forming polymer to enhance strength. Preferred second polymers are alcohol and water soluble with a tensile strength of greater than about 2000 psi and an elongation of greater than about 10%. Solubility of the film-forming polymer in alcohol will ensure chemical compatibility with the binder, and water solubility will assure that the dispersability and dissolution characteristics of the particle are not significantly affected.

Generally, no more than about 0.001–10 wt % of the strength enhancing second film-forming polymer is sufficient to enhance the structural integrity of a particle formed therefrom. Preferably, the second film-forming polymer is used in an amount within the range from about 0.001 wt % to about 5 wt %, even more preferably within the range of 0.1–1 wt %, based on the amount of the binder.

Preferred second film-forming polymers for enhancing the strength of the PEG particle include cellulose derivatives (i.e., hydroxypropyl cellulose, hydroxyethyl cellulose); polyethylene oxide; polyvinylpyrrolidone, and hydroxypropyl guar.

The dissolution rate of the PEG and the associated release rate of the active ingredient can be adjusted by adding an erosion rate modifier to the PEG. See, Snipes U.S. Pat. No. 4,629,621 particularly in column 4, lines 1–10 the disclosure of which is herein incorporated by reference. Suitable erosion rate modifiers include $C_{12}$–$C_{20}$ fatty acids (e.g., lauric acid, myristic acid, palmitic acid, stearic acid, and arachidic acid); $C_{12}$–$C_{20}$ alcohols (e.g., lauryl alcohol, myristyl alcohol, palmityl alcohol, stearyl alcohol, and arachidyl alcohol); amphophilic esters of fatty acids with glycerol (e.g., monoesters of $C_{12}$–$C_{20}$ fatty acids with glyceryl monopalmitate); $C_{12}$–$C_{20}$ amines (e.g., lauryl amine, myristyl amine, palmityl amine, stearyl amine, and arachidiyl amine); and amides of $C_{12}$–$C_{20}$ fatty acids.

Once thoroughly mixed into a homogeneous material, the temperature of the mixed, molten material is lowered in the stirred vessel to a temperature above the solidification temperature of the molten, homogeneously mixed material. Preferably, the temperature is lowered to a temperature of no more than about 5°–15° C. above the solidification temperature. The specific temperature will depend on the particular binder material used as well as any solvents that have been added. Preferably, the encapsulated AI will exhibit a melting point within the range from about 40° C. to about 70° C.

In general, cooling the molten material inside the stirred, jacketed vessel is less expensive and more flexible than constructing a congealing tower or zone that is tall enough to accommodate the required degree of cooling for all possible formulations made by the present invention.

Once cooled to the desired temperature, the molten binder/AI mixture is sprayed downwardly through any droplet forming device (e.g., nozzles or circular disks exhibiting sized holes) into the top of a congealing tower or zone. As the droplets fall through the cooling area, they solidify and form particles of encapsulated AI.

If a solvent has been used to increase loading, the temperature surrounding the device or heated device within the congealing tower should be maintained at a temperature above the flash point of the solvent but below the melting point of the binder. Solvent flashed from the particles can be recovered and reused with conventional vapor recovery systems.

To reduce the occurrences of plugging, the molten binder/AI can be sprayed into a congealing tower through heated nozzles or a heated rotating disk. Preferably, the nozzles or disk are heated to a temperature of at least about 10° C. above the solidification temperature of the binder/AI mixture. In its most preferred form, a stainless steel disk atomizer is heated with a radiant heater located below the disk and directed upwardly against the bottom of the disk. Virtually any other form of heat can, however, be used. The nozzles or disk are preferably heated to a temperature within the range from about 30° C. to about 50° C. while the congealing tower is cooled by an upwardly flowing stream of air at a temperature within the range from about 5° C. to about 20° C. An air diverter is preferably used for shielding the heated nozzles from contact with the rising cool air. In effect, the diverter is used to divide the cooling tower into a heated zone immediately around the droplet forming orifices and a cooling zone around the periphery for cooling the droplets into solid particles.

The air flow rate is selected to produce a falling rate to allow sufficient time for the particle to solidify completely by the time the particle reaches the collection area at the bottom of the tower. For particles with a diameter of about 300–600 μm, a congealing tower height of about 1–2 m is generally sufficient.

Solid product particles can be collected easily because the solids are dry and non-tacky at the exit from the congealing zone. In the laboratory, solid product can be collected on a tarp or mat. Commercial processes may wish to use more efficient collection means with chutes, weighing sections, and automatic packaging devices.

The Methods of Use Encapsulated AI according to the invention can be applied to plant foliage, soil, animal skin surfaces, and anywhere the AI is needed to be effective. For example, herbicides can be applied to upper or lower plant foliage or to soil for preventing plant growth. Systemic insecticides can be applied to soil, and contact insecticides can be applied to soil or other surfaces where the target insects are known to be travel or feed. The particular sims for treatment and specific application method will depend on the AI and its intended effects.

The encapsulated product particles are distributed or dispersed in the presence of moisture to release the encapsulated AI. The binder will begin to dissolve upon contact with water and release the AI therein. As such, the capsules can be distributed as a dry granule that will release the active material upon contact with irrigation water or rain or mixed with cool water in a spray tank.

In conventional practice, the spray tank contains cool water containing one or more adjuvants, surfactants, or other co-applied material and distribution is through conventional spray nozzles. As such, the product capsules should be formed to exhibit a size within the range from about 150 μm to about 1500 μm, preferably a size within the range of 600–100 μm.

Encapsulation of active ingredients according to the invention provides a number of advantages beyond those mentioned above. First, the binder masks strong, offensive, and nauseating odors emanating from the encapsulated active ingredient. Such encapsulation can provide active materials in a more acceptable form for the end user.

Encapsulation according to the invention also provides the active ingredient in a form that significantly reduces a variety of contact and exposure concerns, i.e., inhalation of fine solids, dermal absorption, and eye irritation. This reduction in contact hazard agrees with a recent study concerning drug permeation. See, Hatanaka et al., "Effect of Vehicle on the Skin Permeability of Drugs: Polyethylene Glycol 400-Water and Ethanol-Water Binary Solvents", *J. Controlled Release,* 23,247–260 (1993).

EXAMPLES

Example 1

PEG is used to encapsulate ethion according to the invention using the formulation in Table 1.

TABLE 1

| Component | Concentration (wt %) |
|---|---|
| polyethylene glycol (MW = 3350) | 33 |
| ethion (97% purity) | 63 |
| surfactant | 4 |

Example 2

Captan was encapsulated with PEG according to the invention according to the formulation in Table 2.

TABLE 2

| Component | Concentration (wt %) |
|---|---|
| polyethylene glycol (MW = 3350) | 32 |
| captan (90% purity) | 60 |
| wetting and dispersing agent | 8 |

Test materials are considered to be "mildly irritating" if their maximum average eye irritation score is within 15.0–25.0 and irritation readings at 7 days are "zero." The toxicity classification for a test material ranges from I–IV according to the criteria in Table 3.

TABLE 3

| Category | Criteria |
|---|---|
| I | Corrosive (irreversible destruction of ocular tissue) or corneal involvement or conjunctival irritation persisting through day 21 |
| II | Corneal involvement or conjunctival irritation clearing in 8–21 days |
| III | Corneal involvement or conjunctival irritation clearing in 7 days or less |
| IV | Minimal effects clearing in less than 24 hours |

PEG-encapsulated captan according to the invention was tested for eye irritation in rabbits according to EPA Guidelines No. 81-4 and compared against the eye irritation exhibited by flowable captan solution (40% captan in water containing an inert thickening agent). According to the standard test protocol, nine young adult albino rabbits were exposed to each material by placing 0.1 ml of material into the conjunctival sac of the left eye. Three of the treated eyes were washed with room temperature deionized water for one minute beginning 30 seconds after exposure to the captan. All treated eyes were washed with room temperature deionized water for one minute immediately after recording the 24 hour observation.

The treated animals were examined and evaluated for irritation at 1, 24, 48, and either 68.5 or 72 hours and at 4, 7, 10, 14, 17, and 21 days after treatment. If effects are not seen at 7 days, examination was terminated. Because the PEG-encapsulated captan showed no effects at 7 days, the difference between the 68.5 hour period actually used and the standard 72 hour period did not affect the outcome of the test. A compilation of the raw data appears in Table 4.

TABLE 4

| Condition | Test Material | Time After Exposure 24 hr. | 72 hr. | 7 days | 21 days |
|---|---|---|---|---|---|
| | | NONWASHED EYES | | | |
| Corneal Opacity | Encap. | 3/6 | 0/6 | 0/6 | — |
| | Flowable | 4/6 | 1/6 | 1/6 | 1/6 |
| Iritis | Encap. | 3/6 | 0/6 | 0/6 | — |
| | Flowable | 2/6 | 0/6 | 0/6 | 0/6 |
| Conjunctival redness | Encap. | 6/6 | 4/6 | 0/6 | — |
| | Flowable | 6/6 | 6/6 | 4/6 | 1/6 |
| Conjunctival Chemosis | Encap. | 6/6 | 1/6 | 0/6 | — |
| | Flowable | 6/6 | 6/6 | 4/6 | 0/6 |
| | | WASHED EYES | | | |
| Corneal Opacity | Encap. | 0/3 | 0/3 | 0/3 | — |
| | Flowable | 0/3 | 0/3 | 0/3 | 0/3 |
| Iritis | Encap. | 0/3 | 0/3 | 0/3 | — |
| | Flowable | 1/3 | 0/3 | 0/3 | 0/3 |
| Conjunctival redness | Encap. | 3/3 | 0/3 | 0/3 | — |
| | Flowable | 2/3 | 1/3 | 0/3 | 0/3 |
| Conjunctival Chemosis | Encap. | 3/3 | 0/3 | 0/3 | — |
| | Flowable | 3/3 | 3/3 | 0/3 | 0/3 |

The irritation scoring and toxicity categorization is in Table 5.

TABLE 5

| Material | Avg. Irritation Score | Irritation Rating | Toxicity Category | Comments |
|---|---|---|---|---|
| PEG ENCAP. | | | | |
| Nonwashed | 21.0 | mildly irritating | III | No conjunctival irritation exhibited by any animal at 7 days |
| Washed | 12.7 | mildly irritating | III | |
| FLOWABLE | | | | |
| Nonwashed | 14.5 | mildly irritating | I | corneal opacity and apparent invasion of cornea by blood vessels and conjunctival redness at Day 21 on one animal, conjunctival irritation exhibited by 4/6 animals at 7 days |
| Washed | 10.0 | mildly irritating | III | |

From Table 5, the PEG encapsulated material with 50 wt % captan shows only a Category III toxicity compared to the more hazardous Category I of the flowable form containing only 40 wt % captan. The explanation for the difference is not well understood at present although it is noted that despite the higher average nonwashed eye irritation scores for the PEG encapsulated captan, the encapsulation appears to provide a measure of protection against long term eye irritation and damage from captan.

We claim:

1. A process for encapsulating an agriculturally effective active ingredient by a process comprising the steps:

mixing until homogeneous (a) 50–90 wt % of an agriculturally effective active ingredient with (b) a water-free, molten, film-forming polymer binder that exhibits a viscosity of less than about 1000 cp, wherein said polymer binder is less than 100% water soluble, at least 20% soluble in alcohol, and forms a non-tacky solid at 20° C.; and forming said homogeneous mixture into particles, wherein said agriculturally effective active ingredient is chemically compatible with said filmforming polymer binder.

2. A process according to claim 1 wherein the mixing step comprises:

mixing said agriculturally effective active ingredient with a molten polymer selected from the group consisting of polyethylene glycol and a block copolymer of ethylene oxide and propylene oxide.

3. A process according to claim 1 wherein the mixing step comprises:

mixing an agriculturally effective active ingredient with a molten solution containing melted polyethylene glycol exhibiting a water solubility at 20° C. within the range from about 15 wt % to about 90 wt % and a melting point within the range from about 37° C. to about 64° C.

4. A process according to claim 1 wherein the mixing step comprises:

mixing said agriculturally effective active ingredient with a molten block copolymer of ethylene oxide and propylene oxide.

5. A process according to claim 1 wherein the forming step comprises:

forming said particles by spraying the mixture of binder and active ingredient through nozzles heated to a temperature above the solidification temperature of said homogeneous mixture.

6. A process according to claim 1 wherein the mixing step comprises:

mixing molten polyethylene glycol with an agriculturally effective active ingredient selected from the group consisting of captan, mancozeb, maneb, niram, metiram, zineb, ferbam, chlorothalonil, iprodione, ziram, copper salts, sulfur, ethion, ethyl parathion, diazinon, endosulfan, solid and liquid forms of the carbamates, organophosphates, compounds which break down an insect's digestive tract tissue, zinc, mercury, nicotine, rotenone, neem oil or azadiractin, petroleum oils, endrin, aldrin and its epoxide, dieldrin, heptachlor, DDT, BHC, lindane, chlordane, methoxychlor, DDD, TDE, the polychlorinated biphenyls, Bacillus thuringiensis, entomopathic viruses, trifluralin, paraquat, glyphosate and salts thereof, alachlor, and the phenoxys as well as salts thereof.

7. A process according to claim 6 wherein the mixing step comprises:

mixing molten polyethylene glycol with captan.

8. A process according to claim 7 wherein the mixing step comprises:

mixing molten polyethylene glycol with about 55–80 wt % captan based on total weight.

9. A process for encapsulating an agriculturally effective active ingredient by a process comprising the steps:

mixing a water insoluble, agriculturally effective active ingredient with molten polyethylene glycol until the mixture is homogeneous;

cooling the homogeneous mixture to a temperature above the solidification temperature of said homogeneous mixture; and forming said homogeneous mixture into particles by spraying the cooled mixture into a congealing tower at a temperature below the melting point of said polyethylene glycol.

10. An agriculturally useful composition comprising:

(a) 50–90 wt % of an agriculturally effective active ingredient homogeneously distributed throughout and encapsulated by (b) a water-free, molten, film-forming polymer binder that is about 20–90% water soluble at 20° C., at least 20% soluble in methanol, and which forms a non-tacky solid at 20° C., wherein said agriculturally effective active ingredient is chemically compatible with said filmforming polymer binder and is selected from the group consisting of captan, mancozeb, maneb, niram, metiram, zineb, ferbam, chlorothalonil, iprodione, ziram, copper salts, sulfur, ethion, ethyl parathion, diazinon, endosulfan, solid and liquid forms of the carbamates, organophosphates, compounds which break down an insect's digestive tract tissue, zinc, mercury, nicotine, rotenone, neem oil, azadiractin, petroleum oils, endrin, aldrin and its epoxide, dieldrin, heptachlor, DDT, BHC, lindane, chlordane, methoxychlor, DDD, TDE, the polychlorinated biphenyls, Bacillus thuringiensis, entomopathic viruses, trifluralin, paraquat, glyphosate and salts thereof, alachlor, and the phenoxys as well as salts thereof.

11. A composition as in claim 10 wherein said active ingredient comprises 55–80 wt % captan.

12. A process for encapsulating an agriculturally effective active ingredient by a process comprising the steps:

mixing until homogeneous (a) 50–90 wt % of an agriculturally effective active ingredient with (b) a water-free, molten, film-forming polymer binder that exhibits a viscosity that allows particle formation through nozzles, wherein said polymer binder is less than 100% water soluble, at least 20% soluble in alcohol, and forms a non-tacky solid at 20° C.; and forming said homogeneous mixture into particles.

13. A process according to claim 12 wherein the mixing step comprises:

mixing molten polyethylene glycol with about 55–80 wt % captan based on total weight.

14. A process for encapsulating an agriculturally effective active ingredient by a process comprising the steps:

mixing until homogeneous (a) 50–90 wt % an agriculturally effective active ingredient with (b) a water-free, molten, film-forming polymer binder, wherein said polymer binder is less than 100% water soluble, at least 20% soluble in alcohol, and forms a non-tacky solid at 20° C.; and forming said homogeneous mixture into particles.

15. A process according to claim 14 wherein the mixing step comprises:

mixing molten polyethylene glycol with about 55–80 wt % captan based on total weight.

* * * * *